US007235120B2

(12) United States Patent
Dennis

(10) Patent No.: US 7,235,120 B2
(45) Date of Patent: Jun. 26, 2007

(54) ELECTROSTATIC AEROSOL FILTERING APPARATUS

(75) Inventor: John Hugh Dennis, Shipley (GB)

(73) Assignee: University of Bradford, Bradford, West Yorkshire (GB)

( * ) Notice: Subject to any disclaimer, the term of this patent is extended or adjusted under 35 U.S.C. 154(b) by 135 days.

(21) Appl. No.: 10/476,461

(22) PCT Filed: Apr. 22, 2002

(86) PCT No.: PCT/GB02/01855

§ 371 (c)(1),
(2), (4) Date: Jun. 14, 2004

(87) PCT Pub. No.: WO02/087771

PCT Pub. Date: Nov. 7, 2002

(65) Prior Publication Data

US 2004/0216612 A1 Nov. 4, 2004

(30) Foreign Application Priority Data

May 1, 2001 (GB) ................................ 0110838.0

(51) Int. Cl.
*B03C 3/32* (2006.01)
*B03C 3/68* (2006.01)

(52) U.S. Cl. .......................... 95/2; 95/3; 95/69; 95/78; 96/18; 96/19; 96/57; 96/58; 96/63

(58) Field of Classification Search .................... 96/17, 96/57, 58, 63, 64, 66, 18, 19; 95/2, 3, 69, 95/78

See application file for complete search history.

(56) References Cited

U.S. PATENT DOCUMENTS

| | | | | |
|---|---|---|---|---|
| 2,844,214 | A * | 7/1958 | Hall et al. | 96/66 |
| 4,597,781 | A * | 7/1986 | Spector | 96/52 |
| 4,902,306 | A * | 2/1990 | Burnett et al. | 95/69 |
| 5,037,455 | A * | 8/1991 | Scheineson et al. | 96/17 |
| 5,042,997 | A * | 8/1991 | Rhodes | 96/18 |
| 5,123,936 | A * | 6/1992 | Stone et al. | 95/65 |
| 5,268,009 | A * | 12/1993 | Thompson et al. | 96/67 |
| 5,478,377 | A * | 12/1995 | Scavnicky et al. | 96/17 |
| 5,484,472 | A * | 1/1996 | Weinberg | 96/26 |
| 5,540,756 | A * | 7/1996 | Hoppitt et al. | 95/69 |
| 5,573,577 | A * | 11/1996 | Joannou | 96/66 |
| 5,593,476 | A * | 1/1997 | Coppom | 95/78 |
| 5,607,497 | A * | 3/1997 | Brown | 73/864.71 |
| 5,814,135 | A * | 9/1998 | Weinberg | 96/58 |
| 5,846,302 | A * | 12/1998 | Putro | 96/66 |
| 5,906,677 | A * | 5/1999 | Dudley | 96/17 |
| 6,156,088 | A * | 12/2000 | Cardarelli | 55/385.8 |
| 6,296,692 | B1 * | 10/2001 | Gutmann | 96/62 |
| 6,413,302 | B1 * | 7/2002 | Harrison et al. | 96/63 |
| 6,428,611 | B1 * | 8/2002 | Andolino et al. | 96/25 |
| 2001/0029728 | A1 * | 10/2001 | Massey et al. | 55/471 |

FOREIGN PATENT DOCUMENTS

JP 55-24561 * 2/1980

* cited by examiner

*Primary Examiner*—Richard L. Chiesa
(74) *Attorney, Agent, or Firm*—Adams Evans P.A.

(57) ABSTRACT

A battery (16) drives an electric motor (17) which in turn drives a fan (18). A circuit board (20) controls the operation of the motor and fan to maintain the flow rate. Air is drawn through an inlet (22) and out through a vent (24). Foam discs (32) and (34) may extract particles from the air and an electrostatic filter may attract aerosols in the air.

24 Claims, 1 Drawing Sheet

ELECTROSTATIC AEROSOL FILTERING APPARATUS

This is a national phase application of International Application PCT/GB02/01855, filed Apr. 22, 2002, and claims priority to Great Britain Patent Application No. 0110838.0, filed May 1, 2001. The present invention relates to aerosol filtering apparatus and a method of monitoring or filtering aerosol.

The present invention relates to aerosol filtering apparatus and a method of monitoring or filtering aerosol.

In the known method of analysing aerosol particles in a room, a high resistance filter has air in the room drawn through it. In order to ensure that the aerosol particles are removed, the filter must be extremely fine which results in the filter having a very high resistance. Thus a large pump with a significant power consumption has to be used. Furthermore, operation of the pump is noisy and the apparatus is heavy, bulky and difficult to transport.

It is an object of the present invention to attempt to overcome at least some of the above or other disadvantages.

According to one aspect of the present invention aerosol filter apparatus comprises a unit arranged, in use, to be carried by a person, the unit including an air inlet and an air outlet and power means arranged, in use, to cause air flow from the inlet to the outlet, the unit further including an electrostatic filter through which at least some of the air that passes from the inlet to the outlet is arranged to pass whereby, in use, at least some of any aerosol in the air passing through the electrostatic filter is retained by the electrostatic filter.

The electrostatic filter may be removable from the unit and, alternatively or additionally, may be replaceable in the unit.

The unit may include at least one filter upstream of the electrostatic filter. That upstream filter may be arranged to remove particles passing through that filter of less than 20 μm or less than 15 μm or more than 1 μm or more than 2 μm or in the region of 2.5 μm or in the region of 10 μm. At least two filters may be provided upstream of the electrostatic filter and each of those upstream filters may be arranged to remove different sized particles.

A filter adjacent to the electrostatic filter and upstream of the electrostatic filter may be spaced from the electrostatic filter. Where two filters are located upstream of the electrostatic filter, each of those two filters may be spaced from each other.

The electrostatic filter may be located in a portion that is removable from the unit.

The electrostatic filter may be mounted in a retaining device and that retaining device may be removable from the unit. Any other filter or filters may also be mounted in the retaining device.

The power means may comprise a fan or a pump. The unit may include a battery power source.

According to another aspect of the present invention a method of monitoring the aerosol comprises a user carrying a unit that causes air to pass through an electrostatic filter with the electrostatic filter trapping at least some of the aerosol contained in air passing through the electrostatic filter.

The method may comprise weighing the filter which method may comprise detaching the filter for weighing, for instance before and after air has been caused to pass through the filter. The weight increase of the filter may give an indication of the amount of aerosol in the air. The method may comprise analysing the particles trapped by the electrostatic filter in order to give an indication of the contaminants trapped by the electrostatic filter.

The method may comprise determining the safety of an environment on the basis of the increase in weight of the electrostatic filter or, alternatively or additionally, on the basis of the particles analysed that are trapped by the filter, for instance by comparing the weight gained or the chemical analysis with data that has a predetermined weight gained for a predetermined time or a predetermined chemical or a predetermined amount of chemical for a predetermined period of time above which an area is deemed not to be safe.

The method may comprise controlling the amount of air passing through the electrostatic filter, for instance, by increasing or decreasing the power causing air to be moved through the filter. The method may comprise controlling the amount of air being drawn through the filter in order to maintain the air flow rate through the filter substantially constant.

The method may comprise attaching the unit to clothing of a carrier, for instance by clipping the unit to clothing such as a belt or pocket of a carrier.

The present invention also includes monitoring aerosol when using an aerosol filter apparatus as herein referred to.

The present invention includes any combination of the herein referred to features or limitations.

The present invention can be carried into practice in various ways but one embodiment will now be described by way of example and with reference to the accompanying drawings, in which.

Figure 1:
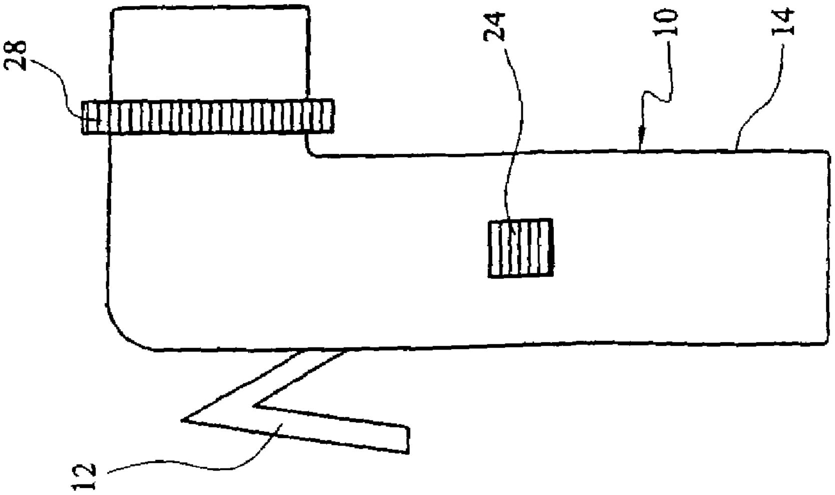
FIG. 1 is a side view of an aerosol filtering unit.
Figure 2:
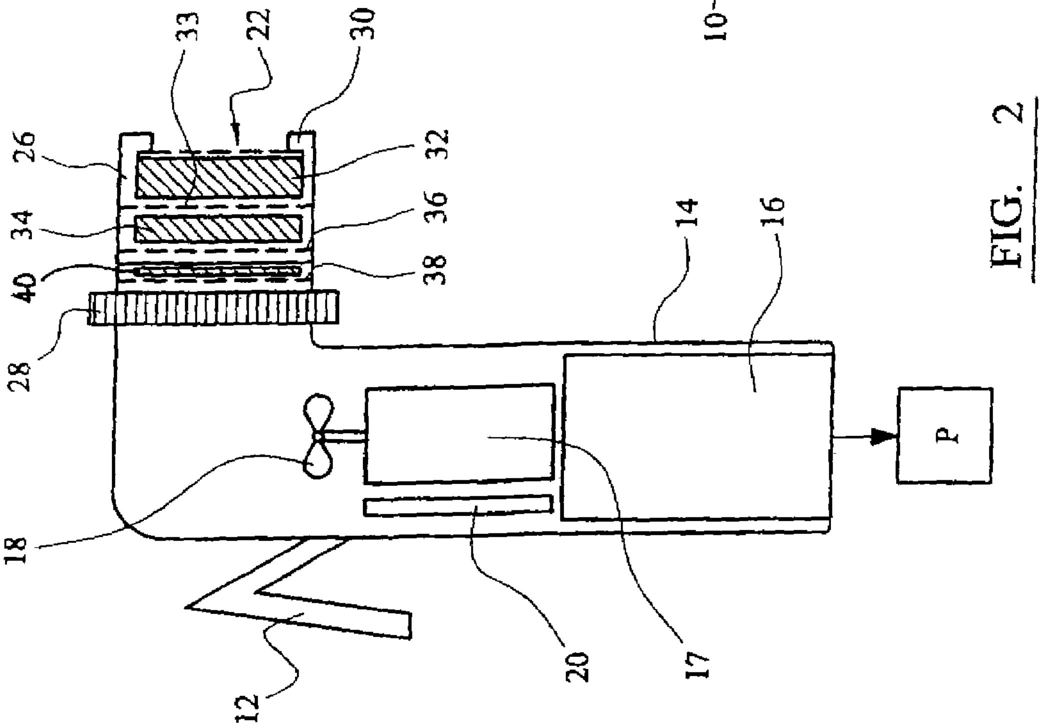
FIG. 2 is a side view similar to FIG. 1 showing the internal components of the unit.
Figure 3:
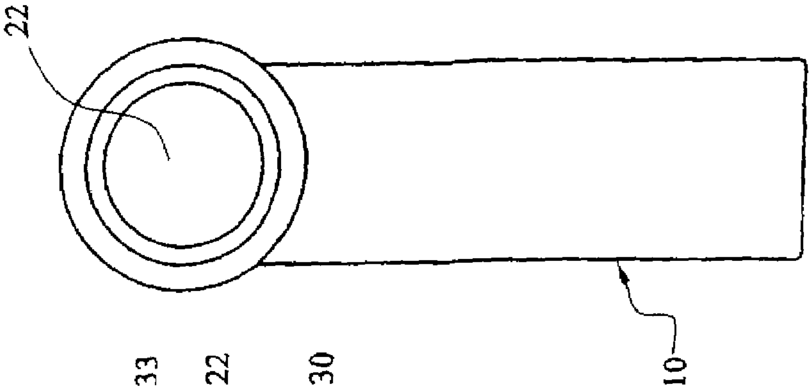
FIG. 3 is a front view of the aerosol filtering unit.

As shown in the figures, the unit 10 includes a clip 12 that enables the unit to be attached to the belt or pocket, for instance, of a person using the unit.

The unit includes a main body 14 housing a battery 16 that drives an electric motor 17 which in turn drives a fan 18. A circuit board 20 controls the operation of the motor and fan, such as by controlling the flow rate or adjusting the power to the fan to maintain the flow rate. The fan 18 pulls air through an inlet 22, through part of the main body 14 and then out through a vent 24. If desired, the battery could be replaced by an external power source (not shown) that directly powers the motor. The fan 18 could be replaced by a pump. The unit may have a low power requirement. The flow rate may be of the order of 22 l/min.

The inlet 22 comprises an open annular end of a cylindrical housing 26 which is detachably mounted on the main body by a securing ring 28. The ring 28 includes an internally threaded portion (not shown) that cooperates with another threaded portion (not shown) on the main body such that as the ring is tightened on the body, an inwardly directed annular flange (not shown) on the ring engages with an outwardly directed annular flange (not shown) on the housing 26 to pull and seal the housing 26 onto the main body 14. The housing 26 can be detached by unscrewing the ring.

The housing 26 includes an inwardly projecting annular flange 30 at its outer end that prevents a relatively thick disc 32 from coming out of the housing. The disc 32 is prevented from moving further into the housing 26 by a grid 33, the other side of which grid 26 supports one side of a further disc 34 of less thickness than the disc 32. Two further grids 36 and 38 are axially spaced from each other, the grid 36 retaining the disc 34 in position and the grids 36 and 38 retaining an absolute or electrostatic filter 40 in place.

The grids, discs and filter 40 may all be removable and replaceable on the housing 26, for instance by sliding them out of the end of the housing remote from the flange 30 when the housing is detached from the main body.

The disc 32 may be a foam disc arranged to remove particles above 2.5 μm and the disc 34 may also be a foam disc arranged to remove particles above 10 μm. The electrostatic filter may be a 3M filtrate media. Both discs and the electrostatic filter can be mounted on a cassette containing the grids for ease of removal or replacement. The grids or the electrostatic filter or any or all of them may be removable and replaceable in the cassette.

The electrostatic filter is made up of loosely packed fibres which contain strong electrostatic charges (usually both positive and negative). When aerosol laden air is drawn through the filter, the aerosols are attracted to the charged fibre and deposit on its surface. Aerosols either have an electrostatic charge or will attain one when drawn through the electrostatic filter. Electrostatic filters can have a very low air flow resistance. Electrostatic filters have a very high efficiency in collecting aerosol particles. Electrostatic filters are more efficient at collecting smaller particles than larger particles. The fibres that make up the electrostatic filter comprise polypropylene with advanced electrolyte with the fibres being rectangular ribbon fibres with a +ve charge on one side and a −ve charge on the other.

In use, a user will clip the unit onto their clothes and walk into a room or outside, for example around a chemical plant. The user may be performing their normal duties or may specifically be testing the atmosphere.

The filters collect dust and any aerosol particles. If desired, all of the filters or any one filter can be weighed to determine the weight gain during use which in turn can be used to determine the level of contamination in an area. For instance an operative could walk around for a predetermined period of time using the filtering unit. Alternatively to the weight analysis, or in addition, any one ore more of the filters, including the absolute or electrostatic filter could have the particles trapped therein analysed to give a chemical assay of the contaminants in an area.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. An aerosol monitoring apparatus comprising a unit (10) arranged, in use, to be carried by a person and to be separate from the respiratory system of the person, the unit including a detachable air inlet (22) and an air outlet (24) and power means (16) arranged, in use, to cause air flow from the inlet to the outlet, the unit further including a replaceable electrostatic filter (40) mounted in the detachable air inlet through which at least some of the air that passes from the inlet to the outlet is arranged to pass whereby, in use, at least some of any aerosol in the air passing through the electrostatic filter (40) is retained by the electrostatic filter, the unit (10) and power means (16) being arranged in use to control the amount of air being drawn through the filter in order to maintain the air flow rate through the filter substantially constant.

2. Apparatus as claimed in claim 1 in which the electrostatic filter (40) is removable from the unit.

3. Apparatus as claimed in claim 1 or 2 in which the electrostatic filter (40) is replaceable in the unit.

4. Apparatus as claimed in claim 1 including at least one filter (32, 34) upstream of the electrostatic filter.

5. Apparatus as claimed in claim 4 in which the upstream filter (32) is arranged to remove particles passing through that filter of less than 20 μm.

6. Apparatus as claimed in claim 4 in which the upstream filter (34) is arranged to remove particles of more than 2 μm.

7. Apparatus as claimed in claims 4, 5 or 6 in which at least two filters (32, 34) are provided upstream of the electrostatic filter each of which are arranged to remove different sized particles.

8. Apparatus as claimed in claim 4 in which the filter (34) is adjacent to the electrostatic filter.

9. Apparatus as claimed in claim 4 in which the filter (32) is spaced from the electrostatic filter.

10. Apparatus as claimed in claim 7 in which the two filters (32, 34) are spaced from each other.

11. Apparatus as claimed in claim 1 in which the electrostatic filter (40) is located in a portion that is removable from the unit.

12. Apparatus as claimed in claim 1 in which the electrostatic filter (4) is mounted in a retaining device.

13. Apparatus as claimed in claim 12 in which the retaining device is removable from the unit.

14. Apparatus as claimed in claim 1 in which the unit includes a battery power source (16).

15. A method of monitoring an aerosol comprising the steps of: (a) a user carrying a unit separate from the respiratory system of the user that causes air to pass through a replaceable electrostatic filter (40) mounted in a detachable air inlet (22); and (b) the electrostatic filter trapping at least some of the aerosol contained in air passing through the electrostatic filter; and (c) controlling (20) the amount of air being drawn through the filter in order to maintain the air flow rate through the filter substantially constant.

16. A method as claimed in claim 15 comprising monitoring the trapped aerosol.

17. A method as claimed in claim 15 or 16 comprising weighing the filter.

18. A method as claimed in claim 16 comprising weighing the filter before and after air has been caused to pass through the filter.

19. A method as claimed in claim 18 in which the weight increase of the filter gives an indication of the amount of aerosol in the air.

20. A method as claimed in claim 15 comprising analysing the particles trapped by the electrostatic filter in order to give an indication of the contaminants trapped by the electrostatic filter.

21. A method as claimed in claim 16 comprising determining the safety of an environment on the basis of the monitoring of the trapped aerosol.

22. A method as claimed in claim 15 comprising determining the safety of an environment on the basis of the increase in weight of the electrostatic filter.

23. A method as claimed in claim 15 comprising determining the safety of an environment on the basis of the particles analysed that are trapped by the filter.

24. A method as claimed in claim 15 comprising attaching the unit to clothing of a carrier.

* * * * *